United States Patent
Ouchi

(10) Patent No.: US 6,299,576 B1
(45) Date of Patent: Oct. 9, 2001

(54) ASSIST TOOL FOR INSERTING A TREATMENT TOOL INTO AN ENDOSCOPE, AND A TREATMENT TOOL TO BE USED IN THE SAME

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/248,268

(22) Filed: Feb. 11, 1999

(30) Foreign Application Priority Data

Feb. 16, 1998 (JP) ................................. 10-031887

(51) Int. Cl.7 ........................................ A61B 1/00
(52) U.S. Cl. ........................ 600/106; 600/104; 606/1
(58) Field of Search ................... 600/104, 105, 600/106, 107, 114, 123, 153, 154; 606/1; 604/164

(56) References Cited

U.S. PATENT DOCUMENTS

| 4,068,659 | 1/1978 | Moorehead . |
| 4,421,382 | 12/1983 | Doi et al. . |
| 4,668,226 | 5/1987 | Omata et al. . |
| 4,826,280 | * 5/1989 | Hiramoto et al. ............... 385/116 |
| 4,829,999 | * 5/1989 | Auth ................................. 606/1 |
| 4,889,106 | * 12/1989 | Watanabe ........................ 600/101 |
| 4,921,479 | * 5/1990 | Grayzel .......................... 604/509 |
| 4,973,329 | * 11/1990 | Park et al. ........................ 606/1 |
| 5,820,546 | 10/1998 | Ouchi . |
| 5,846,181 | 12/1998 | Heckele et al. . |

FOREIGN PATENT DOCUMENTS

| 195 40 731 | 5/1997 | (DE) . |
| 56-37683 | 9/1981 | (JP) . |
| 59-122 | 1/1984 | (JP) . |
| 9-492 | 1/1997 | (JP) . |

* cited by examiner

Primary Examiner—John P. Leubecker
(74) Attorney, Agent, or Firm—Greenblum & Bernstein, P.L.C.

(57) ABSTRACT

An assist tool, which is used to insert a treatment tool used with an endoscope, includes a treatment tool port, an endoscope-connecting portion, and a flexible tube. The treatment tool port is used for inserting the treatment tool into the flexible tube. The endoscope-connecting portion connects the assist tool to the treatment tool insertion channel of an endoscope. The flexible tube connects the treatment tool port to the endoscope-connecting portion. The treatment tool port is formed in an end portion on an operator-side of the assist tool. The endoscope-connecting portion is formed at a tip end of the assist tool. A slit continuously elongates from the treatment tool port to at least a portion of the flexible tube that is located in a vicinity of the endoscope-connecting portion.

9 Claims, 6 Drawing Sheets

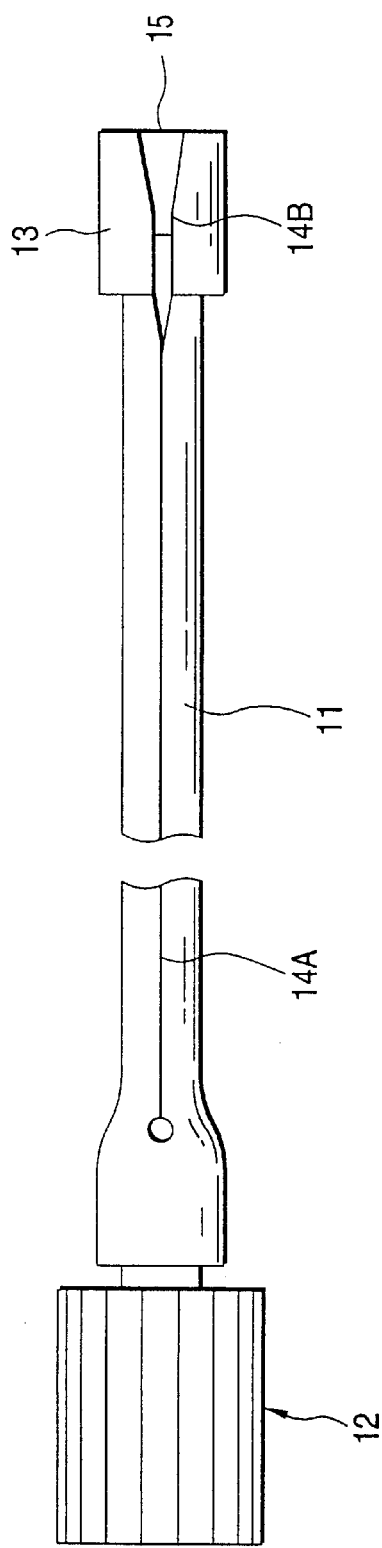
FIG. 3
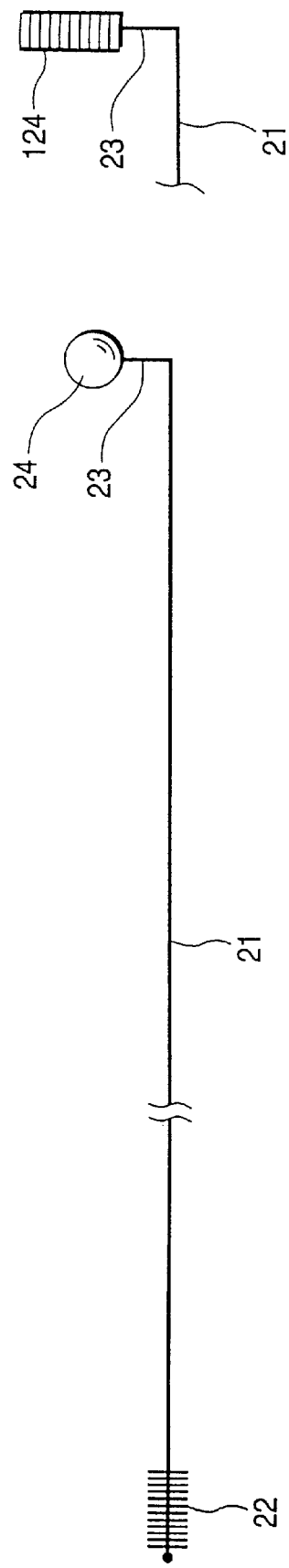
FIG. 4A
FIG. 4B

ASSIST TOOL FOR INSERTING A TREATMENT TOOL INTO AN ENDOSCOPE, AND A TREATMENT TOOL TO BE USED IN THE SAME

BACKGROUND OF THE INVENTION

1. Field of the Invention

The present invention relates to an assist tool that allows a treatment tool to be easily inserted into a treatment tool insertion channel of an endoscope, and also to a treatment tool for an endoscope that is to be used in the assist tool.

2. Description of the Related Art

Usually, a treatment tool for an endoscope has a flexible shaft that is to be inserted into and extracted from a treatment tool insertion channel of an endoscope. The flexible shaft is forcedly inserted into the channel while being nipped by the fingers of an operator. During this operation, the flexible shaft may be easily bent and broken due to its lack of firmness.

Countermeasures against the above-described problems have been proposed. An adapter for restricting a flexible shaft from being bent, so as to allow the flexible shaft to be pushed only in a straight direction has been proposed in Japanese Utility Model Examined Publication No. SHO56-37683. Additionally, a flexible shaft sandwiched between a pair of rollers that are driven by a motor has been proposed in Japanese Patent Unexamined Publication No. HEI9-492.

However, the aforementioned proposals have not been successful in overcoming the above-described problems. The adapter for restricting the flexible shaft from being bent has drawbacks in that it is difficult to smoothly insert or extract the flexible shaft, and the adapter is hardly used. In the motor-driven configuration, the operator cannot sense the movement of the treatment tool, and hence a dangerous situation may arise.

SUMMARY OF THE INVENTION

It is an object of the present invention to provide an assist tool for easily and safely inserting/extracting a treatment tool into/from a treatment tool insertion channel of an endoscope, without the treating tool buckling.

It is also an object of the present invention to provide a treatment tool that is to be used in the assist tool.

In order attain the above objects, an assist tool, which is used to insert a treatment tool used with an endoscope, includes a treatment tool port, an endoscope-connecting portion, and a flexible tube. The treatment tool port is used for inserting the treatment tool into the flexible tube. The endoscope-connecting portion connects the assist tool to the treatment tool insertion channel of an endoscope. The flexible tube connects the treatment tool port to the endoscope-connecting portion. The treatment tool port is formed in an end portion on an operator-side of the assist tool. The endoscope-connecting portion is formed at a tip end of the assist tool. A slit continuously elongates from the treatment tool port to at least a portion of the flexible tube that is located in a vicinity of the endoscope-connecting portion.

The slit may be formed by splitting the flexible tube along an axial direction thereof. Also, the slit may be gradually widened toward an end on the side of the treatment tool port.

At least one of the treatment tool port and the endoscope-connecting portion may be configured by attaching another component to the flexible tube. Alternatively, at least one of the treatment tool port and the endoscope-connecting portion may be configured by the flexible tube itself, or both the treatment tool port and the endoscope-connecting portion may be configured by the flexible tube itself.

The treatment tool for an endoscope according to the present invention includes a flexible shaft, a slit-passing arm and a finger hold. The flexible shaft is inserted into and extracted from a treatment tool insertion channel of an endoscope. The slit-passing arm is laterally protruded from a vicinity of an operator-side end portion of the flexible shaft, and is formed thinly as seen in an axial direction of the flexible shaft. The finger hold is formed at a tip end of the slit-passing arm. The finger hold may have an annular shape, which is centered at the flexible shaft.

BRIEF DESCRIPTION OF THE DRAWINGS

FIG. 3 is a plan view of the assist tool of the present invention;

FIG. 4A is a side view of a treatment tool of the present invention;

FIG. 4B is a side view of a modification of the finger hold shown in FIG. 4A;

DETAILED DESCRIPTION OF THE PREFERRED EMBODIMENTS

Embodiments of the present invention will now be described with reference to the accompanying drawings.

Figure 2:
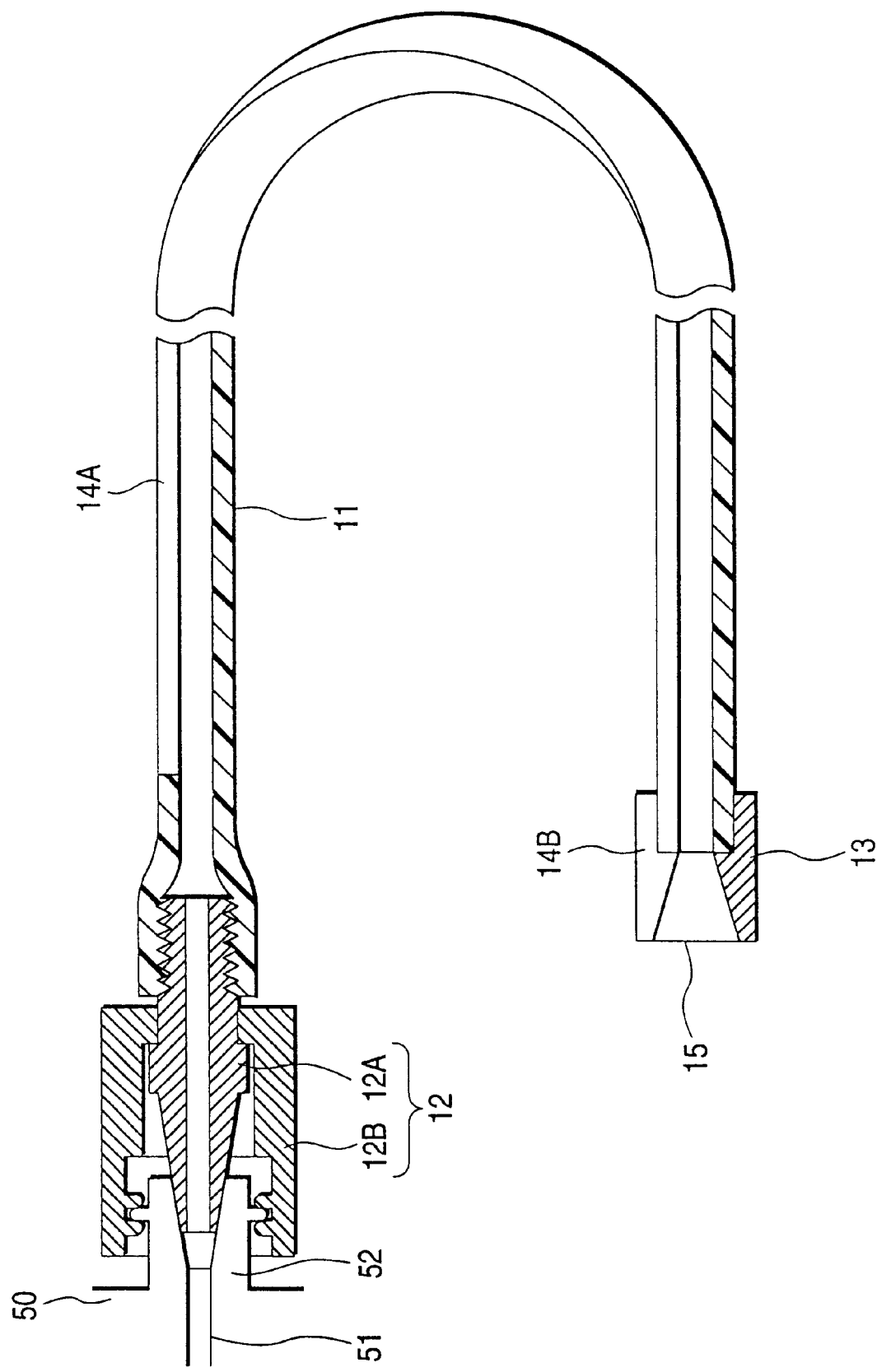
FIG. 2 is a side section view of an assist tool according to the present invention.

FIG. 2 shows an assist tool for inserting a treatment tool for use with an endoscope. An endoscope connector mouthpiece 12 is attached to the tip end of a flexible tube 11, and an operator-side mouthpiece 13 is attached to the end portion on the operator side of the flexible tube 11.

The flexible tube 11 is flexible and pliable, and is made of, for example, polytetrafluoroethylene resin, high-density polyethylene resin, or polyimide resin. However, the flexible tube is firm enough that, when it is connected to a treatment tool insertion mouthpiece 52 of an endoscope, the tube does not hang from the connecting portion.

The endoscope connector mouthpiece 12, which is attached to the tip end of the flexible tube 11, is detachably connected to the treatment tool insertion mouthpiece 52. The treatment tool insertion mouthpiece 52 is in turn disposed in the inlet portion of a treatment tool insertion channel 51 of the endoscope.

The treatment tool insertion mouthpiece 52 protrudes from an operation unit 50 of the endoscope. In the present example, the mouthpiece has the same shape as an injection needle mouthpiece of the so-called Luer-Lok type.

The endoscope connector mouthpiece 12 has the same shape as an injection cylinder mouthpiece of the Luer-Lok type. The mouthpiece 12 is configured by a tapered pipe 12A, which is screwingly coupled to the tip end of the flexible tube 11, and a fixing nut 12B, which is to be screwed with the treatment tool insertion mouthpiece 52.

In the operator-side mouthpiece 13, an inlet hole (i.e., treatment tool port 15) is widened so as to have a funnel-like shape in order to allow a treatment tool to be easily inserted into the flexible tube 11. A treatment tool that is inserted into the flexible tube 11 through the treatment tool port 15 can be fed into the treatment tool insertion channel 51 via the endoscope connector mouthpiece 12.

In the flexible tube 11, a cut slit 14A which elongates from the operator-side end portion to the vicinity of the tip end is cuttingly formed by a razor or the like. As shown in FIG. 3, the tip end portion of the cut slit 14A is formed into a round hole so as to prevent the flexible tube 11 from being torn toward the periphery thereof.

Also in the operator-side mouthpiece 13, a slit 14B is formed so as to communicate with the cut slit 14A of the flexible tube 11. The slit 14B has a substantial width and is opened in the end portion, being further widened into a tapered shape. The basal end portion of the cut slit 14A of the flexible tube 11 is widened into a tapered shape so as to correspond with the width of the slit 14B of the operator-side mouthpiece 13.

FIGS. 4A and 4B show a treatment tool, which is suitably used in the assist tool of the present invention. In this example, the treatment tool is a brush for use with an endoscope. However, the invention may be applied to various other treatment tools that are used with an endoscope.

Reference numeral 21 denotes a flexible shaft configured by a flexible member, such as a stranded metal wire or a coil pipe. A brush 22 (i.e., tip end treatment portion) is attached to the tip end of the flexible shaft 21. The operator-side end portion of the flexible shaft 21 is laterally bent so as to form an L-like shape. A spherical finger hold 24 is attached to the tip end of the end portion. Alternatively, as shown in FIG. 4B, a rectangular finger hold 124 or the like may be used.

In the thus configured treatment tool, when the operator-side end portion of the flexible shaft 21 is positioned in the flexible tube 11, the portion 23 which is laterally bent is passed through the cut slit 14A so that the finger hold 24 is positioned outside the flexible tube 11. Therefore, it is preferable to form the portion (i.e., slit-passing arm 23) so as to be thin as viewed in the axial direction of the flexible shaft 21.

Figure 5:
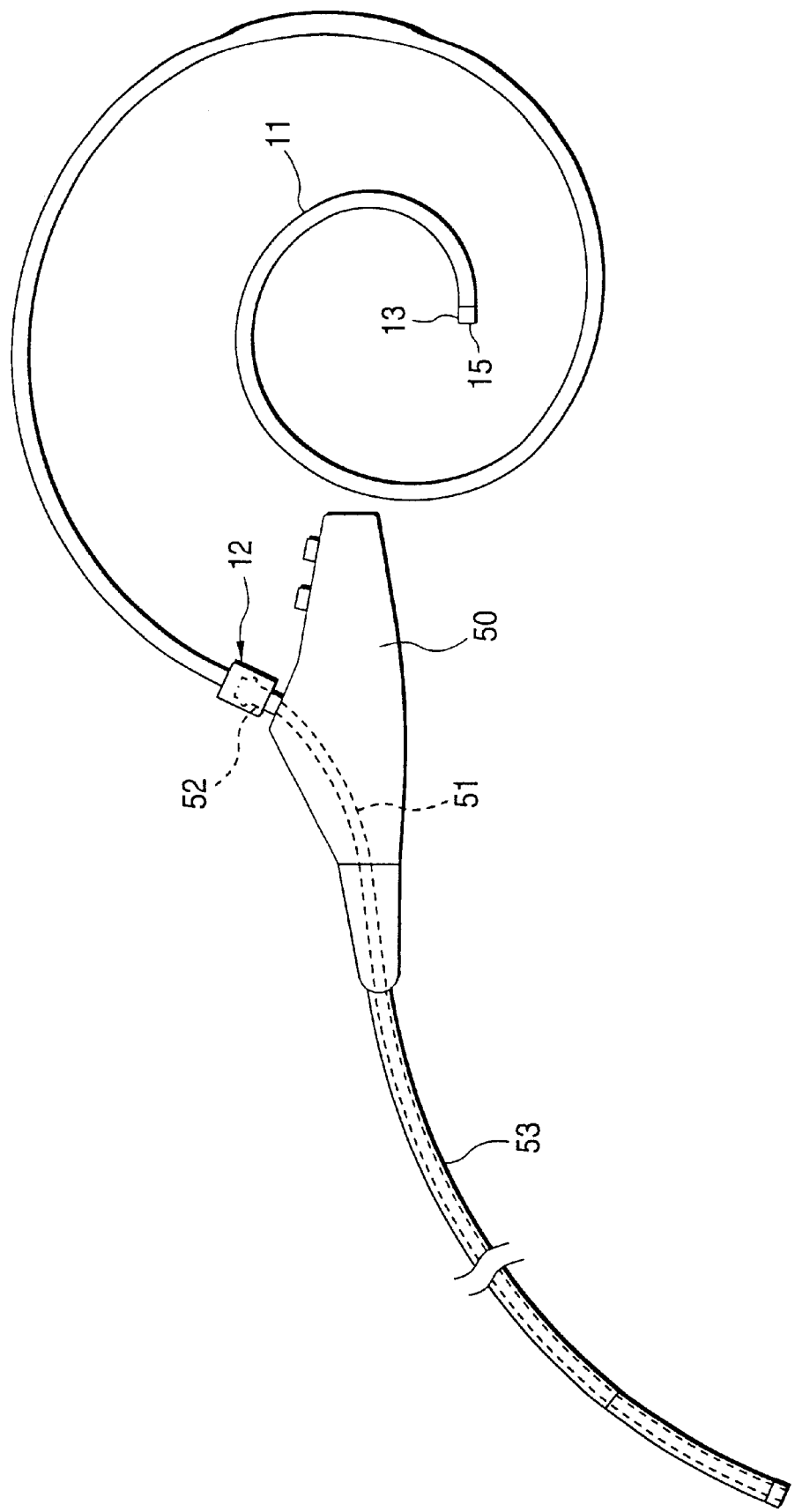
FIG. 5 is an external view showing a state in which the assist tool of the present invention is attached to an endoscope.

FIG. 5 shows a state in which the assist tool for inserting a treatment tool is attached to an endoscope. When the flexible tube 11 is looped, the tube does not occupy a large space. The reference numeral 53 denotes an insertion portion of the endoscope. The insertion portion 53 is sheathed by a flexible pipe.

Figure 1:
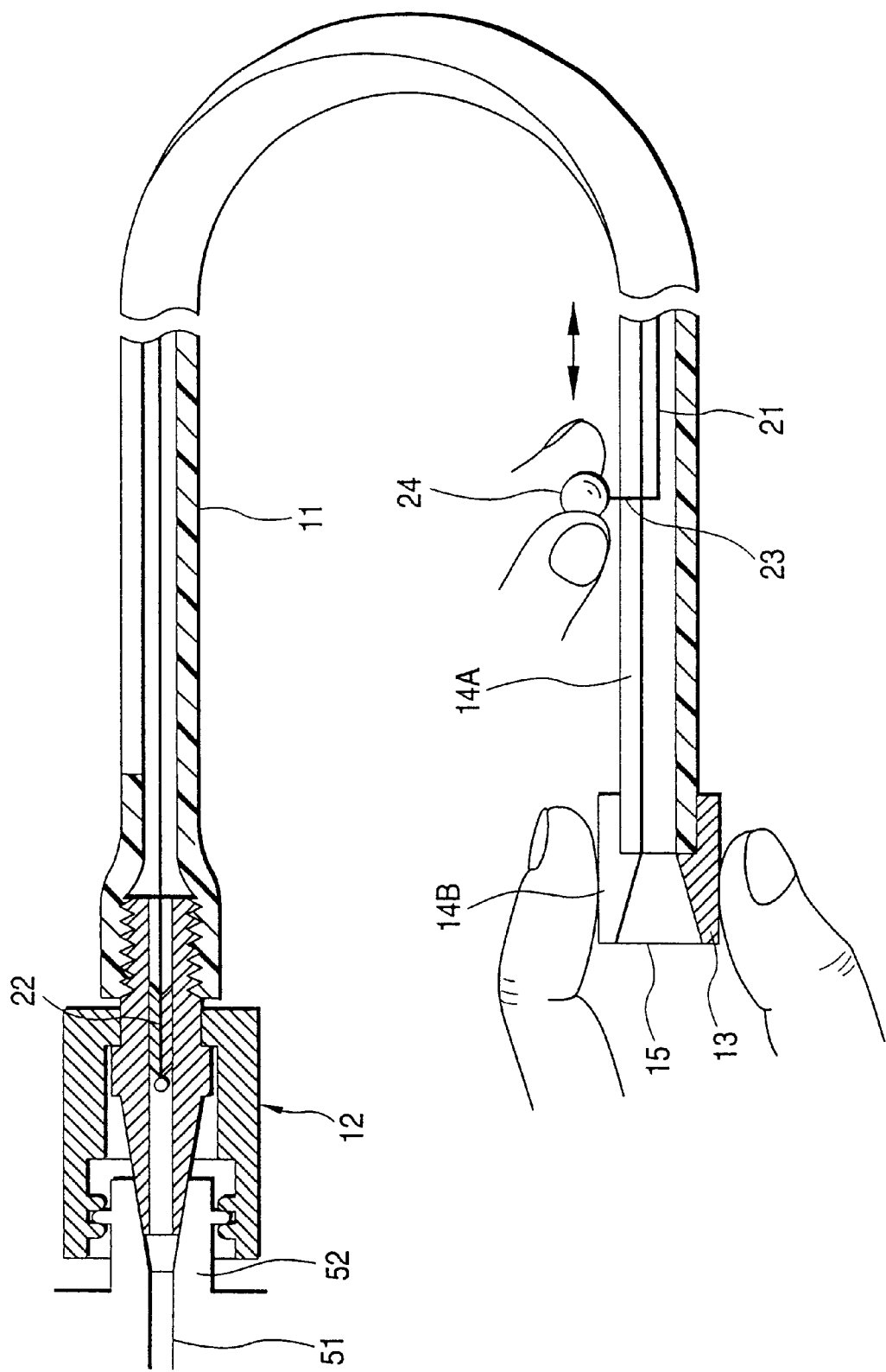
FIG. 1 is a side section view showing a state in which a treatment tool is inserted into an assist tool of the present invention.

FIG. 1 shows a state in which a treatment tool is being inserted into the treatment tool insertion channel 51 using the assist tool of the present invention.

First, the brush 22 at the tip end of the treatment tool is inserted into the treatment tool port 15. Then, the treatment tool is pushed through the flexible tube 11 so as to be eventually inserted into the treatment tool insertion channel 51. In this case, the slit-passing arm 23 of the treatment tool is passed through the slit 14B of the operator-side mouthpiece 13 and the cut slit 14A of the flexible tube 11, so that the finger hold 24 is exposed to the outside.

As shown in FIG. 1, therefore, the operator can hold the operator-side mouthpiece 13 by nipping it with the fingers of one hand, and moving the finger hold 24 along the cut slit 14A by nipping it with the fingers of the other hand. With the above operation, the flexible shaft 21 is slid in the axial direction of the flexible tube 11 so as to be advanced toward the treatment tool insertion channel 51. Since the portion of the flexible shaft 21 located outside the treatment tool insertion channel 51 is surrounded by the flexible tube 11, the flexible shaft 21 can be smoothly and slidingly moved without buckling.

Figure 6:
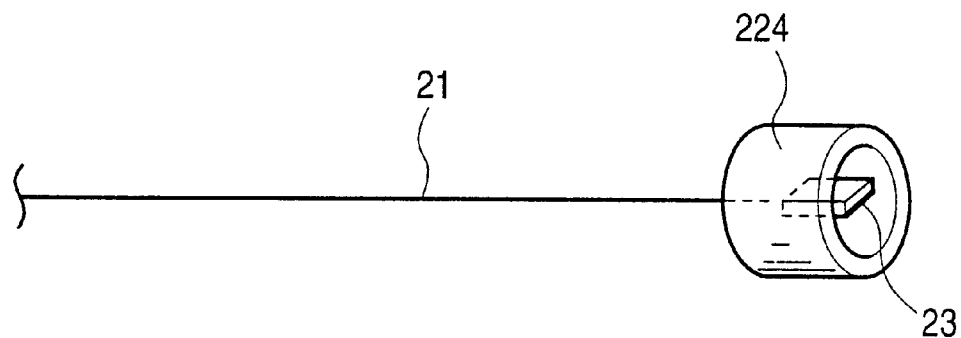
FIG. 6 is a side view showing another example of a treatment tool of the present invention.
Figure 7:
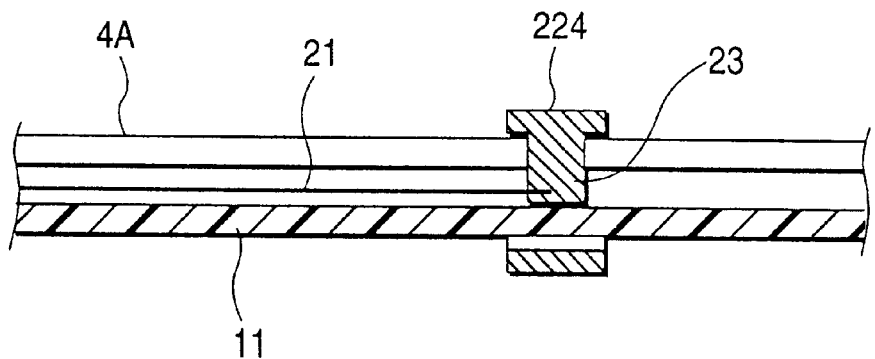
FIG. 7 is a partial side section view showing a state in which the treatment tool of FIG. 6 is inserted into the assist tool.

As indicated by reference numeral 224 in FIG. 6, the finger hold of the treatment tool may be formed into an annular shape that is centered at the flexible shaft 21. During use, as shown in FIG. 7, the exposed finger hold 224 surrounds the outer periphery of the flexible tube 11, and hence can be easily operated.

Figure 8:
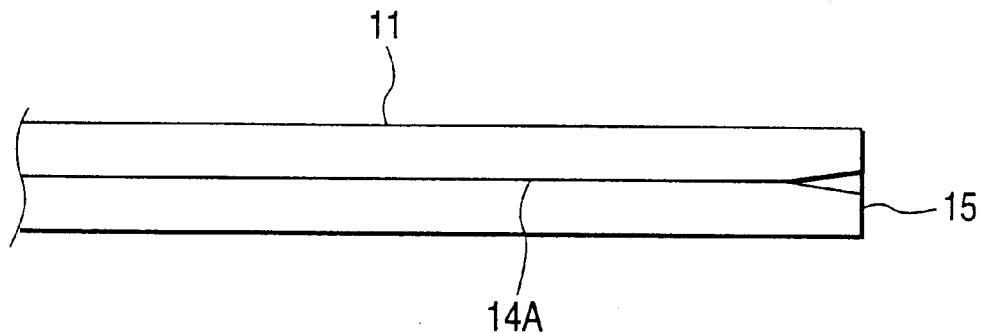
FIG. 8 is a plan view of an operator-side end portion of another example of the assist tool of the present invention.
Figure 9:
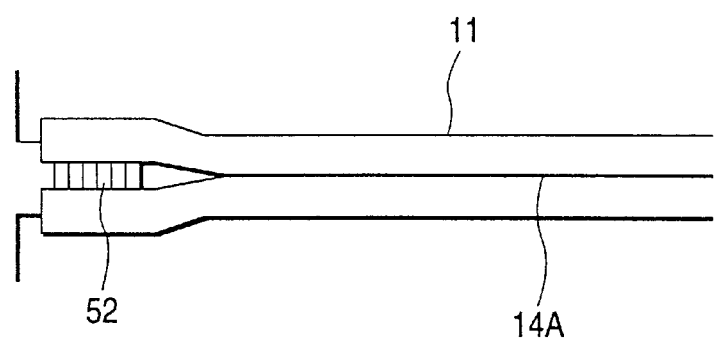
FIG. 9 is a plan view of a tip end portion of another example of an assist tool of the present invention.

In the flexible tube 11, as shown in FIG. 8, the operator-side mouthpiece 13 may be not attached, and the operator-side end portion of the flexible tube 11 may be used as the treatment tool port 15. As shown in FIG. 9, the endoscope connector mouthpiece 12 may be not attached to the tip end of the flexible tube 11, and the tip end of the flexible tube 11 may be directly connected to the treatment tool insertion mouthpiece 52.

Therefore, the assist tool for inserting a treatment tool may be configured by using only one flexible tube 11 in which a cut slit 14A is formed. The cut slit 14A may be formed over the entire length of the flexible tube 11 so as to elongate to the tip end of the flexible tube 11.

Figure 10:
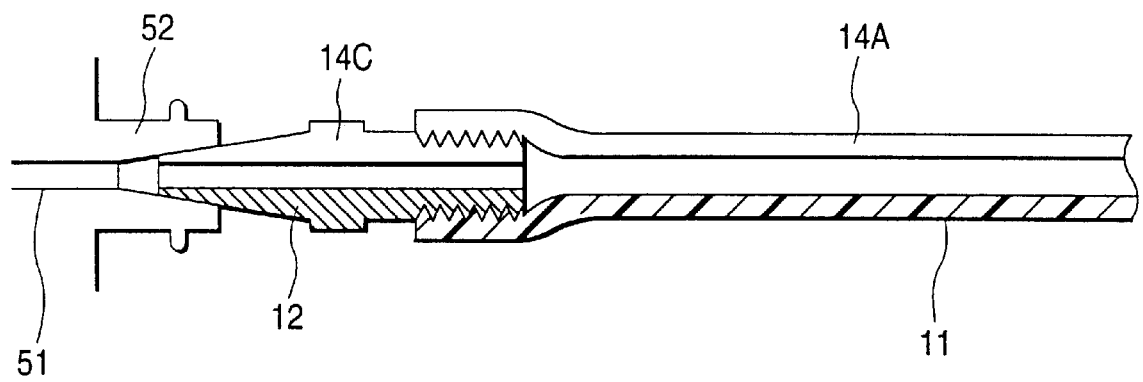
FIG. 10 is a side section view of a tip end portion of yet another example of an assist tool of the present invention.

As shown in FIG. 10, another slit 14C, through which the slit-passing arm 23 of the treatment tool is to be passed, may be formed in the endoscope connector mouthpiece 12 attached to the tip end of the flexible tube 11.

According to the present invention, a slit-passing arm, which protrudes laterally from a basal end portion of a flexible shaft of a treatment tool, is passed through a slit formed in a flexible tube that is to be connected to a treatment tool insertion channel of an endoscope. Additionally, a finger hold formed at the tip end of the slit-passing arm is moved along the slit, whereby the flexible shaft of the treatment tool can be slid in the axial direction of the flexible tube. Outside the treatment tool insertion channel, the flexible shaft is surrounded by the flexible tube. Therefore, the shaft can be smoothly and slidingly moved, without buckling. As a result, the treatment tool can be easily and safely inserted into and extracted from the treatment tool insertion channel of the endoscope.

The entire disclosure of each and every foreign patent application from which the benefit of foreign priority has been claimed in the present application is incorporated herein by reference, as if fully set forth.

While only certain embodiments of the invention have been specifically described herein, it will be apparent that numerous modifications may be made thereto without departing from the spirit and scope of the invention.

What is claimed is:

1. An assist tool for inserting a treatment tool into an endoscope, comprising:

a treatment tool port formed on an operator-side of the assist tool;

an endoscope-connecting portion, formed at a tip end of the assist tool, and connectable to a treatment tool insertion channel of the endoscope;

a flexible tube connecting said treatment tool port and said endoscope-connecting portion; and a guiding slit extending continuously along said flexible tube from said treatment tool port to at least a portion of said flexible tube located in a vicinity of said endoscope-connecting portion, wherein axially extending edges of said flexible tube that define said guiding slit do not overlap during use of said assist tool so as to guide insertion of the treatment tool into the treatment tool insertion channel, wherein said guiding slit gradually widens from said flexible tube toward an operator-side end of said treatment tool port.

2. The assist tool according to claim 1, wherein said slit is formed by splitting said flexible tube along an axial direction.

3. The assist tool according to claim 1, wherein at least one of said treatment tool port and said endoscope-connecting portion is configured by another component attached to said flexible tube.

4. The assist tool according to claim 1, wherein at least one of said treatment tool port and said endoscope-connecting portion is configured by said flexible tube itself.

5. The assist tool according to claim 4, wherein both said treatment tool port and said endoscope-connecting portion are configured by said flexible tube itself.

6. The assist tool according to claim 5, wherein said slit is formed over the entire length of the flexible tube.

7. A treatment tool for use with an assist tool of an endoscope, comprising:

a flexible shaft that is insertable into and extractable from a treatment tool insertion channel of an endoscope;

an arm formed on said flexible shaft, said arm extending laterally from a vicinity of an operator-side end portion of said flexible shaft, said arm being formed thinly as viewed in the axial direction of said flexible shaft, said arm extending through an axially extending guide groove of the assist tool and respective edges of the guide groove not overlapping so as to guide one of insertion and extraction of said treatment tool into the treatment tool insertion channel; and a finger hold formed at a tip end of said arm, wherein said finger hold has an annular shape extending around and centered on said flexible shaft and adapted to extend around an outer periphery of the assist tool, and said arm being connected at one end to said flexible shaft, and at another end to said finger hold.

8. The treatment tool according to claim 7, wherein said flexible shaft has a tool positioned on an end thereof, said flexible shaft and said tool being adapted to be guidedly inserted or extracted from the treatment tool insertion channel by the assist tool.

9. The treatment tool according to claim 8, wherein said finger hold is formed on an end of said flexible shaft opposite to said tool, and is positioned outside and along a length of the flexible tube when said tool and said flexible shaft are positioned within the flexible tube.

* * * * *